United States Patent [19]

Walter

[11] 4,163,822
[45] Aug. 7, 1979

[54] PRESSURE SENSITIVE ADHESIVE MATERIAL AND METHOD OF PREPARATION

[75] Inventor: Brian W. Walter, Bishop's Stortford, England

[73] Assignee: Smith & Nephew Research Limited, Harlow, England

[21] Appl. No.: 708,775

[22] Filed: Jul. 26, 1976

[30] Foreign Application Priority Data

Jul. 29, 1975 [GB] United Kingdom ............... 31616/75

[51] Int. Cl.² .......................... B32B 3/26; B32B 5/18
[52] U.S. Cl. ...................................... 428/304; 156/77; 156/246; 156/332; 156/230; 156/249; 260/29.6 MH; 260/29.6 ME; 427/245; 427/373; 427/385 R; 427/207 C; 427/379; 428/343; 428/355
[58] Field of Search .................. 156/77, 229, 230, 231, 156/332, 238, 249, 246, 209, 289; 427/173, 207 C, 207 D, 245, 246, 373, 385 R, 379; 28/DIG. 1; 264/45.8, 288, 16, 47; 428/136, 304, 137, 343, 159, 355; 260/29.6 MH, 29.6 ME; 128/156

[56] References Cited

U.S. PATENT DOCUMENTS

| | | | |
|---|---|---|---|
| 2,618,580 | 11/1952 | Lancaster | 156/77 |
| 2,940,868 | 6/1960 | Patchell | 428/343 |
| 3,090,694 | 5/1963 | Pereny et al. | 260/29.6 MH |
| 3,121,021 | 2/1964 | Copeland | 128/156 |
| 3,302,501 | 2/1967 | Greene | 28/DIG. 1 |
| 3,484,916 | 12/1969 | Johnstone | 28/72.2 R |
| 3,490,937 | 1/1970 | Pietsch et al. | 427/373 |
| 3,523,846 | 8/1970 | Muller | 428/355 |
| 3,565,982 | 2/1971 | Day | 428/304 |
| 3,719,540 | 3/1973 | Hall | 156/229 |
| 3,819,542 | 6/1974 | Kreider | 260/29.6 ME |

Primary Examiner—John T. Goolkasian
Assistant Examiner—J. J. Gallagher
Attorney, Agent, or Firm—Beveridge, DeGrandi, Kline and Lunsford

[57] ABSTRACT

The present invention provides a process for making a water vapor permeable pressure sensitive adhesive material which comprises forming on a surface which is poorly wettable (or non-wettable) by water, a continuous coating of an aqueous emulsion based pressure sensitive adhesive having dispersed therein a water immiscible organic liquid which is more volatile than water and which does not break the emulsion; leaving the coating at room temperature until pores develop and reach a size such that the material when dried will have a water vapor permeability of from 2000 to 10,000 units as hereinafter defined; drying the coating at a higher temperature and transferring the adhesive mass to a water vapor permeable backing material. The pressure sensitive adhesive material finds use in the medical and surgical fields and especially in first-aid dressings and tapes.

14 Claims, 3 Drawing Figures

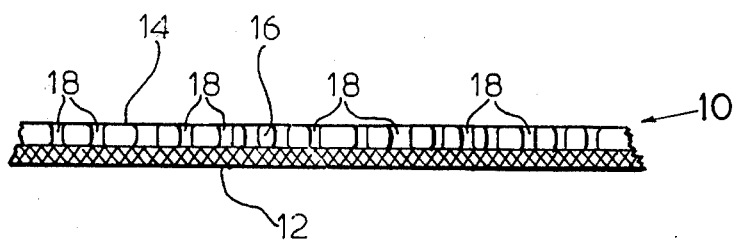
FIG 1
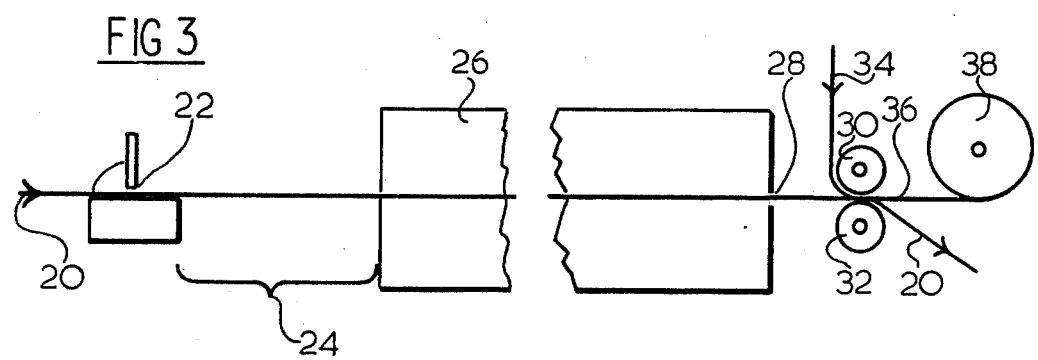
FIG 3
FIG 2
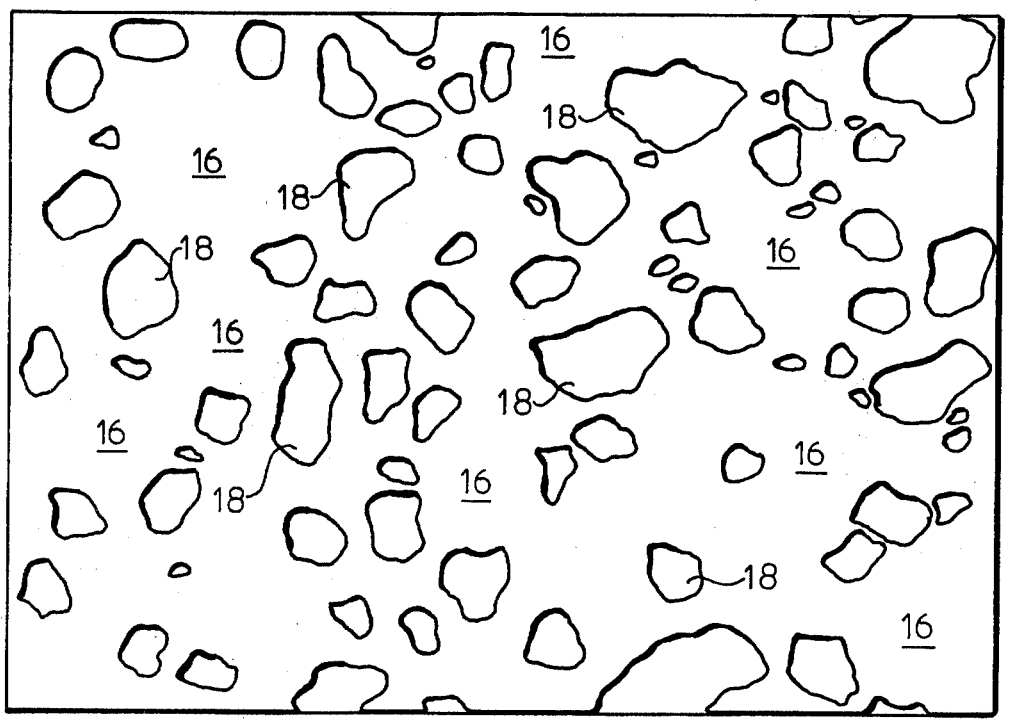

PRESSURE SENSITIVE ADHESIVE MATERIAL AND METHOD OF PREPARATION

The present invention relates to water vapour permeable pressure sensitive adhesive materials and to their production.

It is known to produce a pressure sensitive adhesive material with a non-woven fibre backing, a microporous adhesive being formed in association with the backing by spreading adhesive/solvent mixture thereon and evaporating off the solvent. In such a process the adhesive breaks up into little holes or pores, of a size which is less than 100 microns and is controlled by the backing. It has now been found possible to produce a water vapour permeable pressure sensitive material in which the pore sizes are independent of the backing and in which it is possible to obtain pores of different desired sizes.

According to the present invention there is provided a process for making a vapour permeable pressure sensitive adhesive material which comprises forming on a surface which is poorly wettable (or non-wettable) by water, a continuous coating of an aqueous emulsion based pressure sensitive adhesive having dispersed therein a water immiscible organic liquid which is more volatile than water and which does not break the emulsion; leaving the coating at room temperature until pores develop and reach a size such that the material when dried will have a vapour permeability of from 2000 to 10,000 units as herein defined; preferably an average diameter of at least 100 microns; drying the coating at a higher temperature and transferring the adhesive mass to a water vapour permeable backing material.

Also according to the present invention there is provided a water vapour permeable pressure sensitive adhesive material comprising a water vapour permeable backing material having a porous adhesive coating on at least part of at least one surface of the backing, the pores having an average diameter of at least 100 microns.

The units of water vapour permeability referred to in the present specification are grams/square meter/24 hours at a temperature of 40° C. and a relative humidity difference of 80% and are to be measured by the Payne Cup method, carried out as follows:

10 mls. of distilled water are added to the cup. A 2¼" diameter sample of the material to be tested is clamped above the opening from the cup. Where an adhesive is being tested, this should first be coated onto a highly permeable backing for support. The arrangement is then placed in an air circulating oven at a temperature of 40° C. and relative humidity of 20% for 24 hours. There is, therefore, a difference between the relative humidity inside the cup and the relative humidity outside the cup. The loss of water from the cup is found by weighing. The water vapour permeability is expressed as grams/-square meter/24 hours/40° C./80% RH for the particular material.

By room temperature is meant a temperature at which the organic liquid will evaporate but not the water to any great extent, and therefore depends upon the organic liquid used, but the temperature should not be above 40° C. By higher temperature is meant a temperature at which water is removed from the adhesive mass reasonably quickly and is preferably at least 60° C.

As mentioned above it is possible by means of the present invention to produce pores of different desired sizes. The different sizes of pores depend on the different conditions employed. Such conditions which may be varied include the release properties (e.g. wettability) of the surface, the time allowed for evaporation of the liquid medium and the type of liquid medium. The pore sizes are not related to the backing. It is possible to achieve repeatable desired pore sizes. Even with large pore sizes the product behaves as if it had a uniformity of adhesive on its surface. Pore sizes as low as 30 microns and as high as 600 microns may be achieved.

The pores preferably have an average diameter of from 100 to 600 microns and more preferably have an average diameter of approximately 200 microns. The process of the invention is such that a fairly uniform spread of the pores over the area of the adhesive may be obtained. Also a fairly close spread of pore diameters may be obtained and in most instances the pores are also clean edged.

The adhesive should be hydrophobic, i.e. should not be affected by water. Preferred adhesives are acrylic adhesives, e.g. acrylate ester copolymer pressure sensitive adhesives.

The backing material may be any suitable backing material having the required water vapour permeability (preferably at least 2000 gm/sq. meter/24 hrs/80% RH, more preferably higher) but a particular preferred backing material is a fibrous net backing material) made from a blend (preferably a 5:1 blend) of high density polyethylene and polystyrene blend sheet melt embossed on one side with a pattern of discrete bosses (preferably hexagon bosses at 50 to the inch) in staggered rows and on the other side with transverse grooves (preferably 250 to the inch), this sheet being stretched in the transverse direction (preferably stretched 100% in the transverse direction) to fibrillate the areas between the bosses. The resultant net consists of solid hexagon bosses connected by fibrous areas broken up by the grooved lines. The hexagon bosses in the backing material stand proud of the remaining surface of the backing and in the finished adhesive material this proves useful in that when the material is in a roll the hexagons provide contact with the adhesive of the overlying or underlying section of the material and prevent overall contact and thus adhesion thereby enabling easier unrolling.

Detailed information concerning suitable backing materials appears in U.S. patent application Ser. No. 627,347.

In the process of the present invention a water immiscible organic liquid e.g. a petroleum ether mixture, is dispersed, preferably uniformly or substantially uniformly, into an aqueous emulsion based pressure sensitive adhesive e.g. an aqueous acrylic emulsion, and the mixture coated onto a surface, which is poorly wettable by water, to form a continuous wet coating, which is then allowed to stand at room temperature for a period of time. During this period the organic solvent evaporates forming pores in the coating which gradually increase in size. The increase in size is believed to be caused by the poor wettability of the surface by the emulsion. When the holes have reached a desired size the coating is exposed to a higher temperature, preferably at least 60° C., for example in an oven, which dries and fixes the adhesive and prevents further increase in pore size. The dried adhesive mass is then transferred to an appropriate backing material by normal techniques (i.e. laminating and stripping off the release surface).

Suitable water immiscible organic liquids include petroleum ether (preferably 40/60 petroleum ether), benzene, toluene and ethyl acetate. It is preferable that the water immiscible liquid is absorbed in the dispersed phase of the emulsion.

The surface which is poorly wettable or non-wettable may be any such surface but preferred materials have been found to be various types of paper coated with a silicone release material.

The surface and the viscosity of the coating dispersion should be chosen such that a continuous coating of the coating dispersion may be formed on the surface.

The pressure sensitive adhesive materials of the invention may be used for various medical and surgical purposes and especially may be used for first-aid dressings and tapes. If desired non-adhesive absorbent pads may be attached to part of the adhesive mass.

The adhesive materials of the invention may find special application in cases where repeated application of the adhesive material to the skin occurs e.g. where daily removal of dressings to inspect a wound site is necessary. This is because where such repeated application and removal is necessary it has been found that a higher water vapour permeability is required in the adhesive material, and the adhesive materials of the present invention have an increased water vapour permeability by comparison with similar dressings made up from the same backing and adhesive but having a continuous coating of adhesive rather than a coating having pores.

The invention will now be further described by reference to the following Examples.

EXAMPLE 1

100 parts by weight of an aqueous acrylic emulsion (Rohm & Haas Acrylic Emulsion N580) is homogeneously blended with 25 parts by weight of a 40/60 petroleum ether mixture using a high speed stirrer. A continuous coating 0.006" thick of this resulting mixture was applied to a sheet of silicone coated paper (Steralease 67) using a knife coating technique, the silicone coated paper passing beneath the knife at a rate of 2 ft. per minute. Two feet beyond the knife the sheet entered an oven set between 60° and 80° C., and the coating was thus maintained at room temperature of 1 minute (i.e. 2 feet at 2 feet/min) before passing into the oven. During this 1 minute at room temperature the petroleum ether began to evaporate causing pores to develop, which pores increased in size to an average diameter of 200 microns before the sheet passed into the oven.

After drying and fixing in the oven, the adhesive mass, which had a dry weight of 40 gm/sq. meter, was transferred to a fibrous net backing formed from a 5:1 blend of high density polyethylene and polystyrene sheet melt embossed on one side with a pattern of discrete hexagon bossed (50 to the inch) in staggered rows and on the other side with transverse grooves (250 to the inch) this sheet being stretched 100 percent in the transverse direction to fibrillate the areas between the bosses.

The resultant sheet of pressure sensitive adhesive material was cut to appropriate size and non-adhesive pads added where required.

In order to show the greatly increased water vapour permeability of the adhesive material produced in accordance with this example, a comparison was made with an adhesive material manufactured from the same fibrous backing and adhesive but having a continuous coating of the adhesive mass (i.e. without the formation of pores). The continuous pressure sensitive adhesive material had a water vapour permeability of 800 gms/sq. meter/24 hours/80% RH, whereas the pressure sensitive adhesive material of the present invention had a water vapour permeability of 8,000 gms/sq. meter/24 hrs/80% RH.

EXAMPLE 2

100 parts by weight of an aqueous acrylic emulsion (Rohm & Haas Acrylic Emulsion N580) is homogeneously blended with 25 parts by weight of a 60/80 petroleum ether mixture using a high speed stirrer. A continuous coating 0.006" thick of this resulting mixture was applied to a sheet of silicone coated paper (Steralease 67) using a knife coating technique, the silicone coated paper passing beneath the knife at a rate of 2 ft. per minute. Two feet beyond the knife the sheet entered an oven set between 80° and 100° C., and the coating was thus maintained at room temperature of 1 minute (i.e. 2 feet at 2 feet/min) before passing into the oven. During this 1 minute at room temperature the petroleum ether began to evaporate causing pores to develop, which pores increased in size to an average diameter of 200 microns before the sheet passed into the oven.

After drying the fixing in the oven, the adhesive mass which had a dry weight of 40 gm/sq. meter was transferred to a fibrous net backing formed from a 5:1 blend of high density polyethylene and polystyrene sheet melt embossed on one side with a pattern of discrete hexagon bossed (50 to the inch) in staggered rows and on the other side with transverse grooves (250 to the inch) this sheet being stretched 100 percent in the transverse direction to fibrillate the areas between the bosses.

The resultant sheet of pressure sensitive adhesive material was cut to appropriate size and non-adhesive pads added where required.

In order to show the greatly increased water vapour permeability of the adhesive material produced in accordance with this example, a comparison was made with an adhesive material manufactured from the same fibrous backing and adhesive but having a continuous coating of the adhesive mass (i.e. without the formation of pores). The continuous pressure sensitive adhesive material had a water vapour permeability of 800 gms/sq. meter/24 hours/80% RH, whereas the pressure sensitive adhesive material of the present invention had a water vapour permeability of 8,000 gms/sq. meter/24 hrs/80% RH.

EXAMPLE 3

100 parts by weight of an aqueous acrylic emulsion (Rohm & Haas Acrylic Emulsion N580) is homogeneously blended with 25 parts by weight of a 40/60 petroleum ether mixture using a high speed stirrer. A continuous coating 0.006" thick of this resulting mixture was applied to a sheet of silicone coated paper (Steralease 37) using a knife coating technique, the silicone coated paper passing beneath the knife at a rate of 2 ft. per minute. Two feet beyond the knife the sheet entered an oven set between 60° and 80° C., and the coating was thus maintained at room temperature of 1 minute (i.e. 2 feet at 2 feet/min) before passing into the oven. During this 1 minute at room temperature the petroleum ether began to evaporate causing pores to develop, which pores increased in size to an average diameter of less than 200 microns before the sheet passed into the oven.

After drying and fixing in the oven, the adhesive mass which had a dry weight of 40 gm/sq. meter was transferred to a fibrous net backing formed from a 5:1 blend of high density polyethylene and polystyrene sheet metal embossed on one side with a pattern of discrete hexagon bossed (50 to the inch) in staggered rows and on the other side with transverse grooves (250 to the inch) this sheet being stretched 100 percent in the transverse direction to fibrillate the areas between the bosses.

The resultant sheet of pressure sensitive adhesive material was cut to appropriate size and non-adhesive pads added where required.

In order to show the greatly increased water vapour permeability of the adhesive material produced in accordance with this example, a comparison was made with an adhesive material manufactured from the same fibrous backing and adhesive but having a continuous coating of the adhesive mass (i.e. without the formation of pores). The continuous pressure sensitive adhesive material had a water vapour permeability of 800 gms/sq. meter/24 hours/80% RH, whereas the pressure sensitive adhesive material of the present invention had a water vapour permeability of 8,000 gms/sq. meter/24 hrs/80% RH.

EXAMPLE 4

100 parts by weight of an aqueous acrylic emulsion (Rohm & Haas Acrylic Emulsion N580) is homogeneously blended with 25 parts by weight of a 40/60 petroleum ether mixture using a high speed stirrer. A continuous coating 0.006" thick of this resulting mixture was applied to a sheet of silicone coated paper (Steralease 37) using a knife coating technique, the silicone coated paper passing beneath the knife at a rate of 2 ft. per minute. Two feet beyond the knife the sheet entered an oven set between 60° and 80° C., and the coating was thus maintained at room temperature of 1 minute (i.e. 2 feet at 2 feet/min) before passing into the oven. During this 1 minute at room temperature the petroleum ether began to evaporate causing pores to develop, which pores increased in size to an average diameter of 200 microns before the sheet passed into the oven.

After drying and fixing in the oven, the adhesive mass which had a dry weight of 40 gm/sq. meter was transferred to a microporous PVC backing (PORVIC).

The resultant sheet of pressure sensitive adhesive material was cut to appropriate size and non-adhesive pads added where required.

EXAMPLE 5

Human volunteers were submitted to tests of the effect of applying to them strips of pressure sensitive adhesive material. A strip of the adhesive material was applied to the inside of an upper arm of a volunteer. After 24 hours the strip was removed, examined for evidence of skin stripping and a fresh strip of the same adhesive material applied to the same area of the arm as previously tested. After a further 24 hours this second strip was removed, the skin examined and a third strip applied. The test was continued for four days. Severe skin stripping was considered to have occurred when removal of the strip produced removal of sufficient skin to lead to exudation from the stripped area.

The strips tested were as follows:

I—a known commercial microporous adhesive strip

II—a strip coated by a continuous spreading process at 40 gm./sq. meter with the acrylic emulsion of Example 1.

III—a strip having a coating of the acrylic emulsion of Example 1 applied thereto by the method of the present invention, also at a rate of 40 gm./sq. meter.

The results are as follows:

Trial 1

| Type of Strip | Number of volunteers exhibiting severe skin stripping. | |
|---|---|---|
| | I | II |
| Day 1 | 0 | 1 |
| Day 2 | 0 | 6 |
| Day 3 | 1 | 10 |
| Day 4 | 1 | 15 |

Trial 2

(30 volunteers)

| Type of Strip | Number of volunteers exhibiting severe skin stripping. | |
|---|---|---|
| | I | III |
| Day 1 | 0 | 0 |
| Day 2 | 0 | 1 |
| Day 3 | 1 | 2 |
| Day 4 | 4 | 3 |

The invention will now be further described by reference to the accompanying drawings in which:

FIG. 1 is a side view of an adhesive material in accordance with the present invention.

FIG. 2 is a plan view of an adhesive material in accordance with the invention, and FIG. 3 is a diagrammatic representation of the process of the invention.

Referring now to FIGS. 1 and 2 there is shown an adhesive material 10 comprising a backing material 12 having an adhesive coating 14 thereon comprising areas of an adhesive material 16 and pores 18 formed in the adhesive coating. In FIG. 2 an approximate indication of the size of the holes is given by the scale. In the arrangement of FIG. 2 the frequency of holes is approximately 9 mm$^{-2}$, the average hole size is approximately 0.031 mm$^2$ (i.e. circle of radius 100$\mu$) and the total pore area is approximately 28 percent of the total area of the adhesive coating.

Referring now to FIG. 3 there is illustrated a diagrammatical process in accordance with the invention. Release-coated paper 20 is fed to a spreading station 22 at which an adhesive mass is applied to the surface of the release coated paper. The release coated paper having the adhesive mass thereon then passes through an area 24 at which it is maintained at room temperature. The release coated paper having the adhesive mass thereon then passes into an oven 26 at a temperature of at least 60° C. During the passage through the oven the coat is dried. After emerging from the oven at 28 the release coated paper having the dried adhesive mass thereon passes into a pair of nip rolls 30, 32. A backing material 34 is also passed between the nip rolls in contact with the adhesive coating 14. On emerging from the nip rolls 30, 32 the release coated paper 20 is stripped from the adhesive coating 14 leaving the adhesive coating 14 attached to the backing layer 34. This adhesive material 36, comprising the backing material 34 and the adhesive coating 14 is wound on to a reel 38 for further processing e.g. cutting to size, attachment of non-adhesive absorbent pads etc. or for storage.

We claim:

1. A process for making a water vapor permeable pressure sensitive adhesive material, which comprises
   (A) forming on a surface, which is poorly wettable (or non-wettable) by water, a continuous coating of an aqueous emulsion based pressure sensitive adhesive having dispersed therein a water immiscible organic liquid, which is more volatile than water and which does not break the emulsion;
   (B) leaving the coating at room temperature until pores develop and reach an average diameter of at least 100 microns;
   (C) drying the coating at a higher temperature of at least 60° C.; and
   (D) transferring the adhesive mass to a water vapor permeable backing material; wherein said water immiscible organic liquid is a petroleum ether mixture.

2. A process for preparing a water vapor permeable, pressure sensitive adhesive material, said process comprising:
   (A) forming on a silicone surface a continuous coating of an aqueous emulsion consisting essentially of a hydrophobic, acrylic, pressure sensitive adhesive copolymer and absorbed in the dispersed phase of said emulsion a water immiscible petroleum ether, which is more volatile than water and which does not break the emulsion;
   (B) maintaining said coating at a first temperature not above about 40° C. to cause said petroleum ether to evaporate, thereby forming pores substantially uniformly distributed throughout said coating, and wherein said silicone surface is sufficiently nonwettable or sufficiently poorly wettable by said emulsion to thereby result in an increase in size of said pores to about 100–600 microns during said evaporation;
   (C) raising the temperature of said coating to a second temperature of at least about 60° C. to dry said coating and to substantially prevent further increase in said pore size; and
   (D) transferring the resulting adhesive mass to a water vapor permeable backing material;
   wherein said coating, when dry, has a water vapor permeability of from 2,000 to 10,000 units.

3. Process according to claim 2 wherein said pores have an average diameter of about 200 microns.

4. Process according to claim 3 wherein said backing material has a water vapor permeability of at least about 2000 gm/sq. meter/24 hrs/80% RH.

5. A process as claimed in claim 1, in which the coating is dried at said higher temperature when the pores reach an average diameter of from 100 to 600 microns.

6. A process as claimed in claim 1, in which the backing material has a water vapor permeability of at least 2,000 units.

7. A process as claimed in claim 1, in which the aqueous emulsion based pressure sensitive adhesive is an aqueous acrylic emulsion.

8. A process as claimed in claim 1, in which non-adhesive absorbent pads are attached to part of the adhesive mass.

9. A process as claimed in claim 1, in which the backing material is a fibrous net backing material made from a blend of high density polyethylene and polystyrene blend sheet metl embossed on one side with a pattern of discrete bosses in staggered rows and on the other side with transverse grooves, this sheet being stretched in the transverse direction to fibrillate the areas between the bosses.

10. A pressure sensitive adhesive material prepared by a process as claimed in claim 1.

11. A process for preparing a water vapor permeable, pressure sensitive adhesive material, said process comprising:
    (A) forming on a surface a continuous coating of an aqueous emulsion-based pressure sensitive adhesive having dispersed therein a water immiscible organic liquid, which is more volatile than water and which does not break the emulsion;
    (B) maintaining said coating at a first temperature not above about 40° C. to cause said organic liquid to evaporate, thereby forming pores in said coating, and wherein said surface is sufficiently nonwettable or sufficiently poorly wettable by said emulsion to thereby result in an increase in size of said pores to about 30–600 microns during said evaporation;
    (C) raising the temperature of said coating to a second temperature of at least about 60° C. to dry said coating and to substantially prevent further increase in said pore size; and
    (D) transferring the resulting adhesive mass to a water vapor permeable backing material; wherein said coating, when dry, has a water vapor permeability of from 2,000 to 10,000 units.

12. Process according to claim 11, wherein said pore size is about 100 to about 600 microns, and wherein said pores are substantially uniformly distributed throughout said coating.

13. Process according to claim 11, wherein said adhesive is a hydrophobic, acrylate ester copolymer pressure sensitive adhesive.

14. A process as claimed in claim 11, in which the surface which is poorly wettable or non-wettable is paper coated with a silicone release material.

* * * * *